United States Patent [19]

Dechene et al.

[11] 4,074,184
[45] Feb. 14, 1978

[54] NONCONDUCTIVE VAPOR/SOLID OR LIQUID FRACTION DETERMINATION

[75] Inventors: Ronald L. Dechene, Boxford; Frank G. Grimaldi; Robert E. Newton, both of Tewksbury, all of Mass.

[73] Assignee: Auburn International, Inc., Danvers, Mass.

[21] Appl. No.: 770,821

[22] Filed: Feb. 22, 1977

Related U.S. Application Data

[63] Continuation-in-part of Ser. No. 719,196, Aug. 31, 1976, and Ser. No. 722,168, Sept. 10, 1976.

[51] Int. Cl.² .................................... G01N 27/42
[52] U.S. Cl. .......................... 324/30 R; 324/61 R
[58] Field of Search ............ 73/61 R, 304; 324/61 R, 324/29, 30 R, 30 B, 30 A, .5 B, .5 AH

[56] References Cited

U.S. PATENT DOCUMENTS 3,639,835 2/1972 Dammig ............................ 324/61 R Primary Examiner—M. Tokar Attorney, Agent, or Firm—Jerry Cohen

[57] ABSTRACT

The relative amounts of liquid phase versus vapor phase of a mixed phase nonconductive fluid such as oil or fuel; or the relative amounts of solids versus gas of a mixed flow of nonconductive particles and gas such as pneumatically conveyed plastic pellets and other material is determined by capacitive measurement taken in several distributed directions overlapping within the cross section of a flow path by providing a rotating electric field therein with an alternating voltage on the order of 10-100 kilohertz, with capacitive measurement produced by the rotated field being proportional to the liquid or solid fraction (and by subtraction from unity, vapor or gas fraction), the rotating electrical field being produced by sequentially rotating the electrical position of six plates equally spaced around the periphery of the cross section to be measured, the plate structure and insulations defining a flow measuring cross section or being spaced on the outer periphery of a nonconductive flow tube with allowance for rigors of flow conditions and fluid environment to provide reliable, long life.

9 Claims, 16 Drawing Figures

NONCONDUCTIVE VAPOR/SOLID OR LIQUID FRACTION DETERMINATION

CROSS REFERENCE TO RELATED APPLICATIONS

This application is a continuation-in-part of our co-pending U.S. application, Ser. No. 719,196, filed Aug. 31, 1976, and of Robert Newton's copending U.S. application Ser. No. 722,168, filed Sept. 10, 1976, and both being of common assignment herewith, the disclosures of which are incorporated herein by reference as though set out at length herein.

BACKGROUND OF THE INVENTION

The present invention relates to measuring relative fractions of liquid (nonconductive) and vapor, or solids (nonconductive) and gases; such as occurs in fuel or oil pumping or pneumatic conveying of solid particles.

The prior art includes a number of mechanical and electrical approaches to the problem limited principally in their failure to deal effectively with the non-homogeneous character of the vapor and liquid or solid and gas mixture across the cross section of a conduit in most practical applications. See also the following references:

1. LeTourneau, B. W., and Bergles, A. E., Co-Chairmen of a Symposium on "Two-Phase Flow Instrumentation," 11th National ASME/AIChE Heat Transfer Conference, Minneapolis, Minn. 1969.
2. Hewitt, G. F., "The Role of Experiments in Two-Phase Systems with Particular Reference to Measurement Techniques," Progress in Heat and Mass Transfer, Vol. 6, 1972, p. 295.
3. Subbotin, V. I., Pakhvalov, Yu. E., Mikhailov, L. E., Leonov, V. A., and Kronin, I. V., "Resistance and Capacitance Methods of Measuring Steam Contents," Teploenergetika, Vol. 21, No. 6, 1974, p. 63.
4. Olsen, H. O., "Theoretical and Experimental Investigation of Impedance Void Meters," Kjeller report KR-118, 1967.
5. Ørbeck, I., "Impedance Void Meter," Kjeller report KR-32, 1962.
6. Maxwell, J. C., "A Treatise on Electricity and Magnetism," Clarendon Press, Oxford, 1881.
7. Bruggeman, D. A. G., "Berechnung Verschiedener Physikalischer Konstanten von Heterogenen Substanzen," Ann. Phys., Leipzig, Vol. 24, 1935, p. 636.
8. Hewitt, G. F., and Hall-Taylor, N. S., "Annular Two-Phase Flow," Pergamon Press, 1970, p. 153.
9. Jones, O. C., Jr., and Zuber, N., "The Interrelation Between Void Fraction Fluctuations and Flow Patterns in Two-Phase Flow," Int. J. Multiphase Flow, Vol. 2, 1975, p. 273, as well as our prior U.S. applications stated above. In particular, the latter discloses a measured conductivity variation to determination of mixed flow conditions and is embodied in the commercially available Auburn International Inc. model 1080 and 1075 instruments.

It is an important object of the invention to provide vapor and liquid fraction of nonconductive gas and solids fraction measurement in a mixed flow dealing effectively with the non-homogeneous cross section profile of such mixtures.

It is a further object of the invention to achieve the measurement over a relatively short length of conduit and not be adversely affected by the spiraling effect of annular flow.

It is a further object of the invention to provide a long lived apparatus dealing with environmental conditions such as thermal expansion and contraction and pressure in an effective way providing long reliable life operation consistent with one or more of the preceding objects.

It is a further object of the invention to provide a simple construction making a minimal disturbance on the system being measured consistent with one or more of the preceding objects.

It is a further object of the invention to screen out sources of spurious readings consistent with one or more of the preceding objects.

It is a further object of the invention to provide an economical device consistent with one or more of the preceding objects.

SUMMARY OF THE INVENTION

In accordance with the invention, capacitance measurements are made sequentially across the cross section of the flow to be measured in a distributed, and preferably non-overlapping sequence. The capacitance measurements in each step of the sequence are summed and the sequence steps controlled by logically counting the capacitance measurement excitation high frequency at a rate which is high in respect to the flow rate through the sensor so that the solids or liquid is essentially standing still for purposes of the measurements to be summed. The frequency of the excitation applied for capacitance measurement is from 10–100 KHZ, preferably 30 KHZ (greater than common power frequencies but lower than radio frequencies). A sensor element comprising multiple electrode sets applies voltage field across the fluid flow and is responsive to capacitance therein. The summed varying capacitive response currents from the sensor are converted to a voltage signal, amplified and displayed on a meter as % solids or liquid. The electrodes for capacitance measurements are preferably a peripheral array of plates oriented around the flowing fluid material of a conduit being monitored, preferably without breaking through the conduit wall or entering or otherwise disturbing or touching the fluid flow.

By utilizing an electrically transparent (non-conductive) section of the flow tube, the sensor may accomplish the subject monitoring from outside the flow tube. The sensor housing preferably comprises a pair of semi-circular tube sections which clamp around outer periphery of the flow tube. Each semi-circular section may comprise a laminated assembly containing sensor plates on the inner surface, an intervening insulator layer and an external ground plane surface. The ground plane surface contains coaxial connectors through which electrical connection to each sensor plate is accomplished.

The sensor is thus readily moveable for monitoring several locations in the system and being totally external to the site piping. Portability or repair is ensured without interrupting site operation. Further, this ability to monitor flowing materials from outside the flow system yields the most economic and reliable sensor with regard to sensor materials and operation.

The figures show the commercially available Auburn International Inc. model 1090 instrument.

DETAILED DESCRIPTION OF PREFERRED EMBODIMENTS

Figure 1:
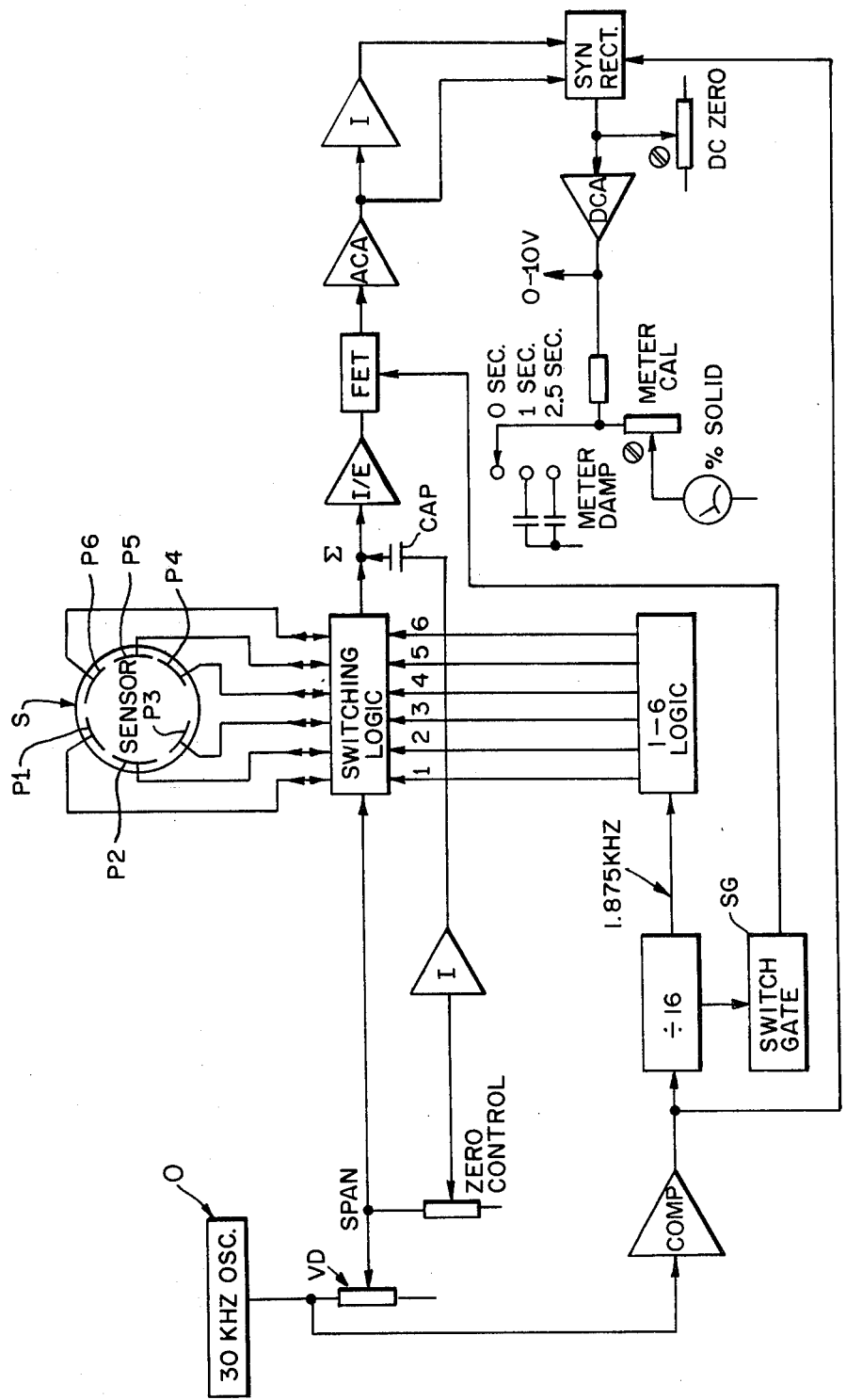
FIG. 1 is a block diagram of the measurement system in accordance with a preferred embodiment of the invention.
Figure 2C:
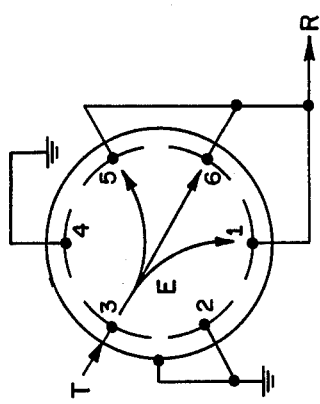
FIGS. 2A-2F are a series of diagrams showing the sequential rotation of the electric field within the sensor.
Figure 2F:
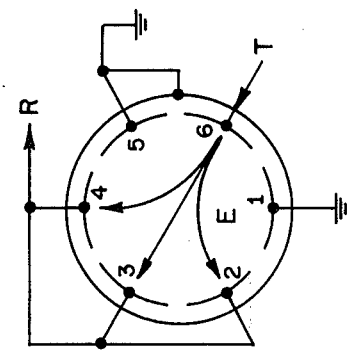
Figure 2B:
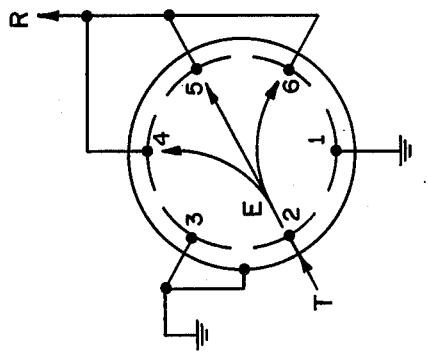
Figure 2E:
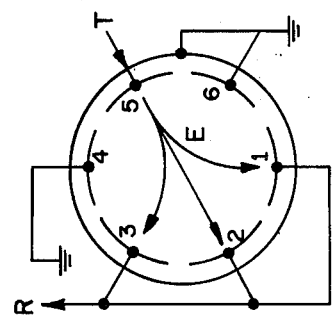
Figure 2A:
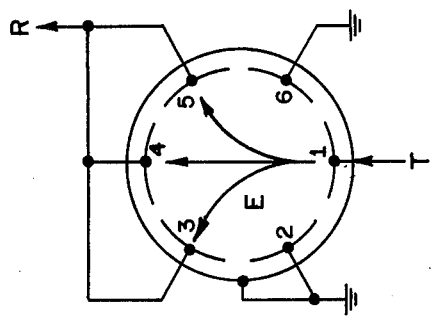
Figure 2D:
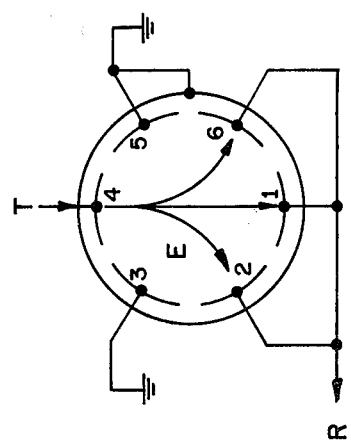

Referring to FIG. 1, a preferred embodiment of the invention comprises a sensor assembly S with multiple electrode plates P1-P6 therein, connected via a span control comprising a voltage divider VD, Comparator COMP and switching logic elements A, B to an oscillating voltage source 0; a summing junction $\Sigma$; and metering elements some being analogous to those described in the above cited applications. The oscillator 0, preferably a Wien Bridge oscillator, produces a stable 30 KHZ sine wave output. The 30 KHZ is applied to the SPAN control and the comparator COMP. The comparator COMP (an operational amplifier) produces a square wave output from 0-5 volts with the transitions at each axis crossing of the 30 KHZ. The output of the comparator is divided by 16 and then converted to a 1 through 6 decimal sequence in LOGIC X which in turn controls the switching sequence of the sensor plates via LOGIC Y.

The output of the SPAN control is connected to the appropriate sensor plate through the Switching Logic and also feeds the ZERO control with a low impedance drive. The output of the ZERO control is inverted and reduced in level and applied through a capacitor CAP as a zeroing current to the Summing Junction ($\Sigma$). The ZERO control is connected after the SPAN control to minimize interaction between zero and span adjustments. The appropriate sensor plates are also connected to the summing junction. The algebraic sum of currents at the summing junction is converted to a voltage by the I to E converter (I/E).

A field effect transistor (FET) is employed to cut off the signal during sequence transitions to prevent the pulses which occur during transition from saturating the following amplifier. The ac amplifier (ACA) provides signal amplification and the inverter (I) inverts the signal so that synchronous rectification via element SYN. RECT. can be employed to derive a DC signal. The output of comparator COMP provides switching input and clocking input for the synchronous rectification. The DC amplifier provides a 0-10V output proportional to solids or liquid in the line as well as driving the front panel meter M. For operation convenience 1 or 2½ second time constant damping is provided for the meter. The DC ZERO control is used to offset any DC components present in the signal.

Referring to FIGS. 2A-F, the six diagrams show the steps 1-6 of the voltage field rotation sequence. In each step a 30 KHZ voltage is applied to plate "T", the three opposing plates are connected together to form a common receiving plate "R" from which a capacitive current proportional to the average dielectric constant within the sensor can flow to ground and the intervening plates are connected to ground to separate the transmit (T) and receive (R) plates. The outer jacket of the sensor is also connected to ground to act as a shield (guard) around the sensor. Since one position would not provide adequate electric field distribution for averaging the dielectric constant of the entire cross section of the sensor; the switching logic advances the electrical position of each plate in a continuous six step sequence; thus rotating the field to achieve good averaging. The peripheral spread of the field at the (R) plates approaches 180° and is in any event substantially above 90° which it should be to avoid fringing errors requiring great correctional effort.

Figure 3:
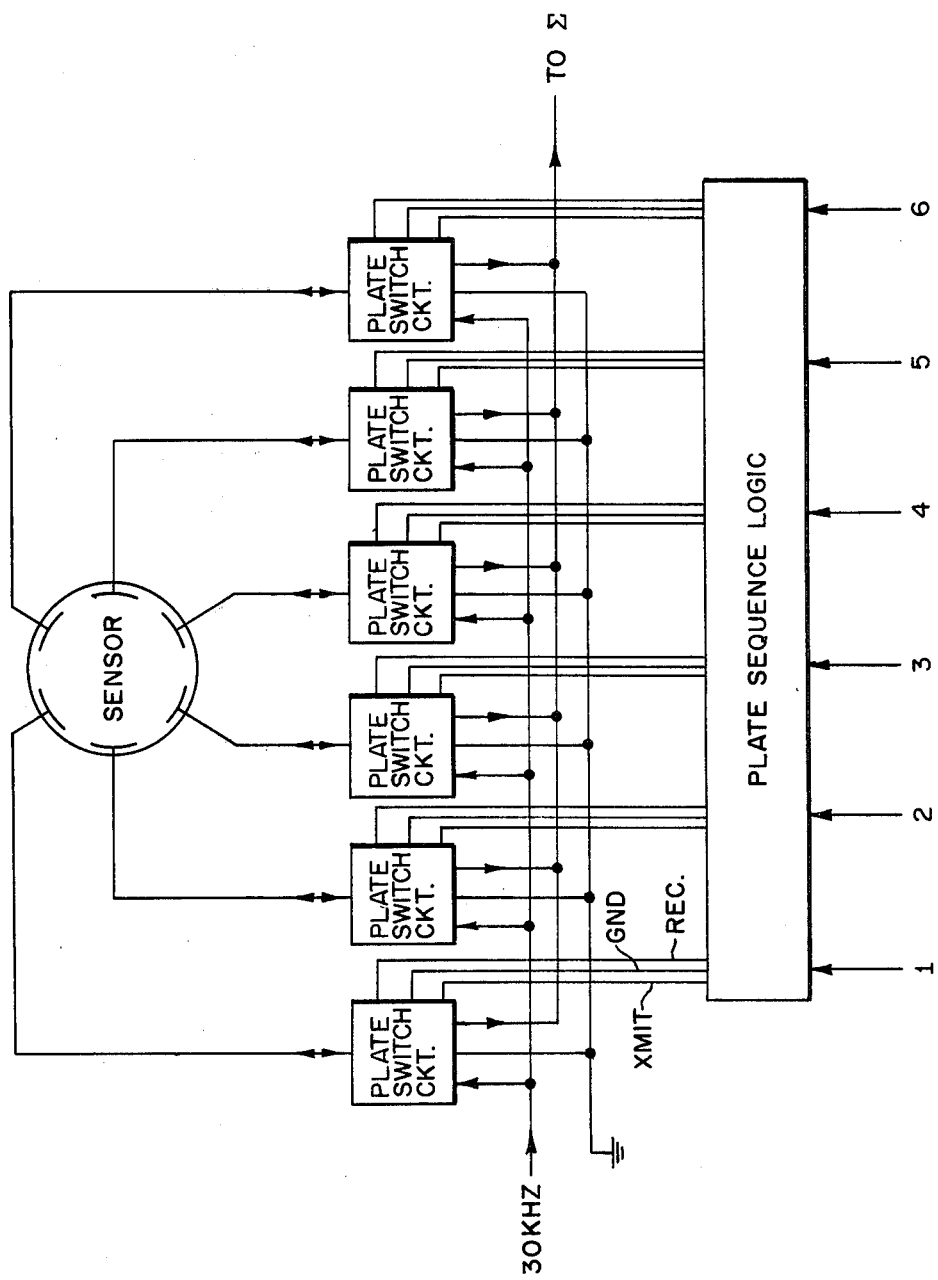
FIG. 3 is a block diagram which shows the "Switching Logic" of the FIG. 1-2 embodiment in greater detail (each sensor plate being connected to 30 KHZ, ground or the Summing Junction ($\Sigma$) through a "plate Switch Circuit", the circuit for each plate being identical).
Figure 4:
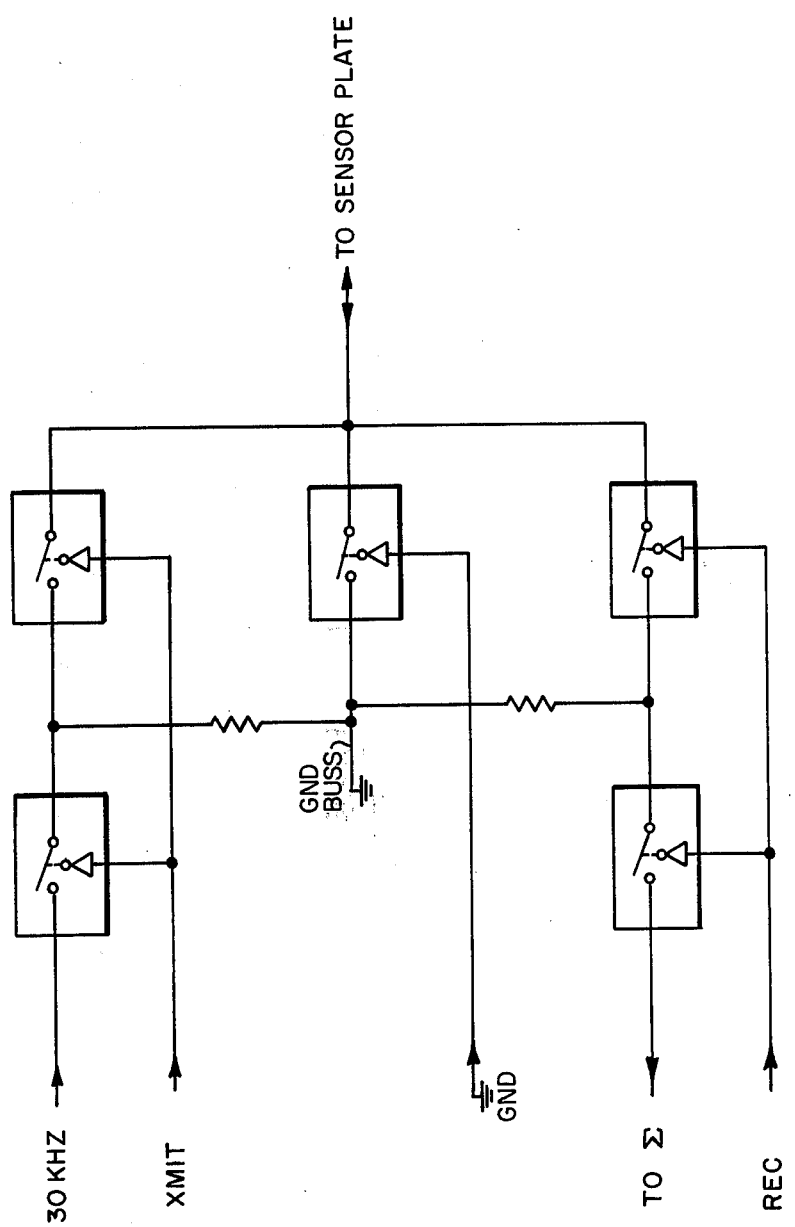
FIG. 4 is an expanded diagram of the plate Switch Circuit element contained in FIG. 3.
Figure 5:
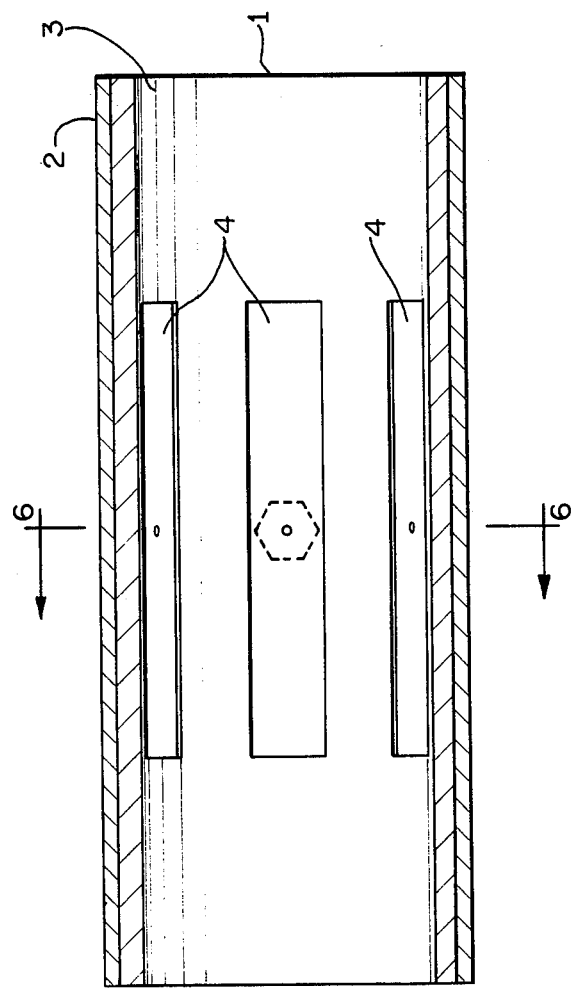
FIGS. 5-6 are, respectively, longitudinal front and cross section views of a sensor instrument portion usable with the FIG. 1-4 instrument.
Figure 6:
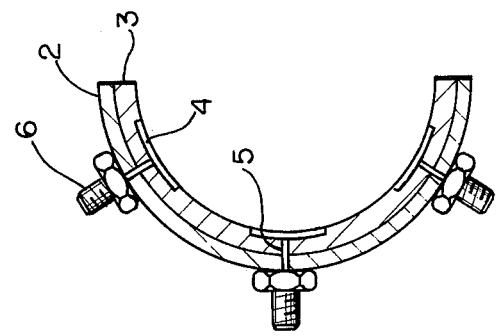
Figure 7:
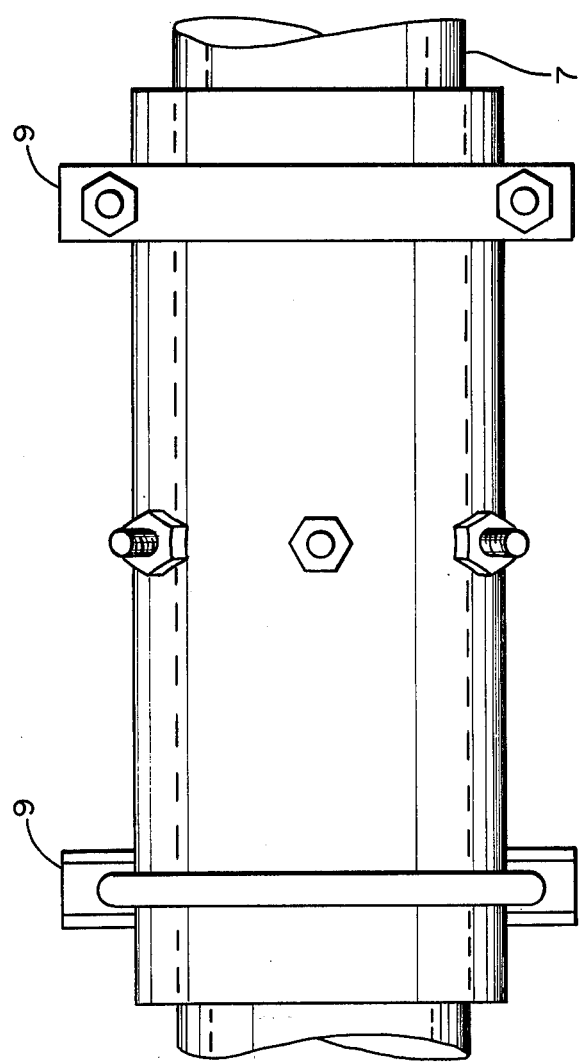
FIGS. 7-8 are longitudinal and cross section views of a flow conduit with the FIGS. 5-6 apparatus applied thereto.
Figure 8:
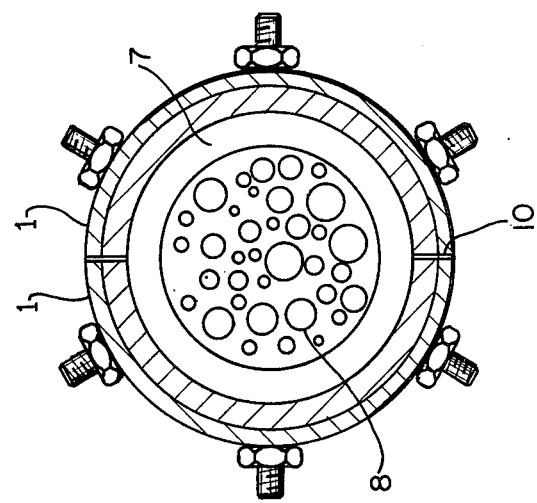

Referring now to FIGS. 3-4, the logic is shown wherein FIG. 4 is a plate switch circuit, six of which are used in the FIG. 3 circuit to selectively interconnect the sensor plates to the oscillating voltage source 0 summing junction $\Sigma$ or to the ground buss. The "plate Sequence Logic" generates the Xmit, Gnd and Rec. logic levels for each plate switch circuit from the 1-6 sequence.

FIG. 4 is a diagram of the "plate Switch Circuit." The circuit consists of five FET switches; two are connected in series with an intermediate load resistor to ground for both the 30 KHZ (T) and $\Sigma$ (R) to isolate the plate when not connected. The remaining FET switch is used to connect the plate to ground.

The applied oscillations of this invention are preferably single-phase and at generally higher frequency compared to the patent applications cited above. The effective plate area is maximized as shown in 2A-2F for signal strength dealing effectively in submicrofarad capacitance values involved. The spatial overlapping patterns produced as shown in FIGS. 2A-2F should provide a "first capacitance plate" with a spread of at least 90°, preferably approaching 180°, of arc, while the opposing "second capacitance plate" is limited to less than 90° opposing the first plate to avoid predominant annular concentration of high strength field and V channel field centrally. Distinct sequence commutation steps (with intervening osolation) of field rotation established a scan of the whole flow cross section and an individual cross section place within the flow is fully scanned several times while flowing axially down the conduit. This rotational scanning contrasts with the known capacitance spiral meters. Capacitance instrument for measuring void fraction in fuel lines and the like in the effective coverage (of the former) of the central core of the flow channel and in effectively counteracting adverse effects of annular flow.

Figure 9A:
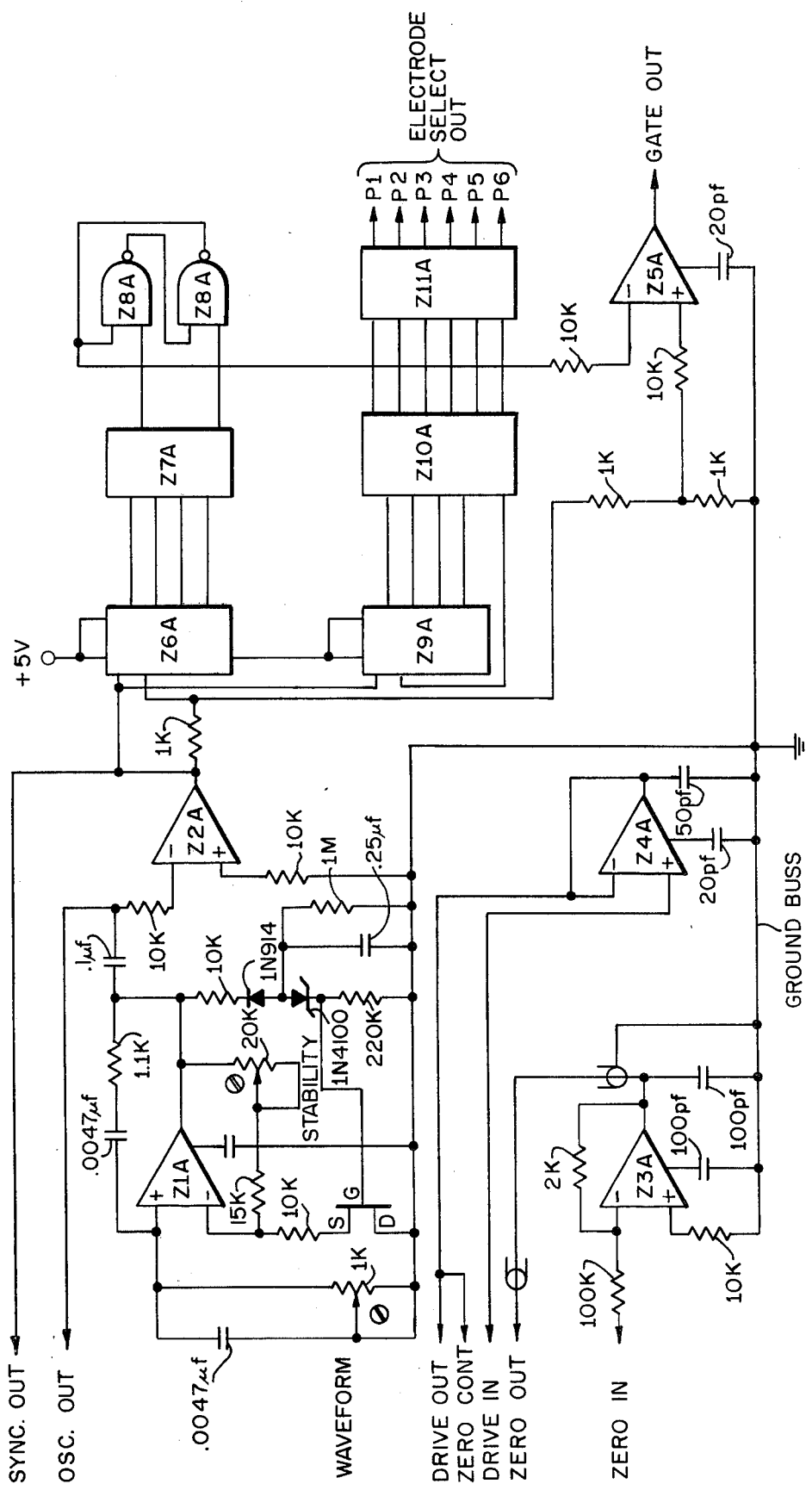
FIGS. 9A-9C are electrical schematic diagrams of the major circuit assemblies incorporated in the FIG. 1 system.

The FIG. 1 system comprises Driver Board, Switching Board and Receiver Board circuits. FIG. 9A is the schematic of the Driver Assembly Operational amplifier Z1A and its associated circuitry form a stabilized Wien Bridge (frequency and amplitude stable capacitance-resistance bridge) oscillator with automatic gain control. The output of the oscillator is fed to the comparator Z2A (shown as COMO in FIG. 1) which produces a square wave output from 0-5 volts with transitions at the axis crossing points of the sine wave generated by the oscillator. Also, the output of the oscillator is coupled to the SPAN control (FIG. 1). The output of the SPAN is connected to the non-inverting input of operational amplifier Z4A (FIG. 1A) which is connected as a non-inverting follower to provide isolation for the SPAN control and a low impedance drive to the ZERO control (FIG. 1) and sensor drive via the Switching Assembly (FIG. 9C below). The output of the ZERO control is inverted and reduced in level by operational amplifier Z3A and is fed to the Receiver Assembly as a zeroing input. The ZERO control is connected after the SPAN control to minimize interaction between the zero and span adjustments.

The output of the comparator is fed to the Receiver Assembly as a switching input for synchroneous rectification. Also, the output is connected as a clock input to two four-stage shift register counters (Z6A and Z9A). The output of Z6A at terminal SYNC. out is 30 KHZ divided by 16 or 1.875 KHZ and is also fed to the input of Z9A. The parallel BDC outputs of the four stages of Z9A are connected to a binary to decimal converter Z10A which generates a one to six sequence which is inverted by the Hex Inverter Z11A and is then fed to the Switching Assembly via the ELECTRODE SELECT OUT CONNECTIONS. A seventh count of Z10A is connected back to the "reset" input of Z9A thus bringing the decimal count back to position one.

The parallel output of Z6A is decoded to a 0-16 decimal count by Z7A. Two NAND gates of a Quad NAND gate Z8A are connected as a latch. When the "15" count from Z7A is reached, the latch is set and when the "2" count is reached the latch is reset. The output of the latch is connected to operational amplifier Z5A which is connected as a Schmidt Trigger thus producing the GATE OUT output which is fed to the Receiver Assembly (FIG. 1C and text below) as a commutation blanking gate signal.

Z1A – Z5A amplifiers are preferably Harris HA2-2625-5 operational amplifiers except Z4A which is a national 311 comparator. The other Z elements are standard logic chips.

Figure 9B:
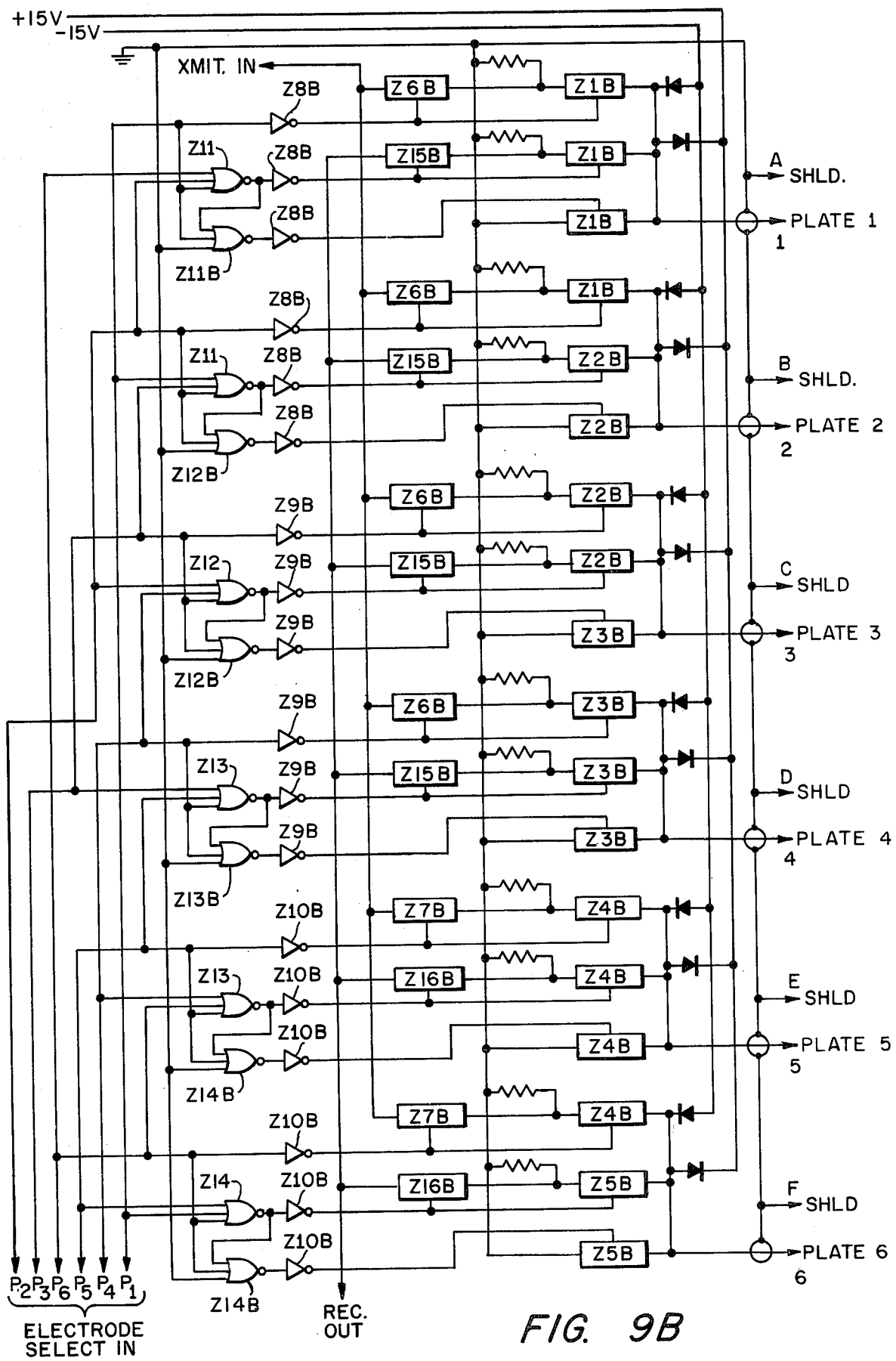
Figure 9C:
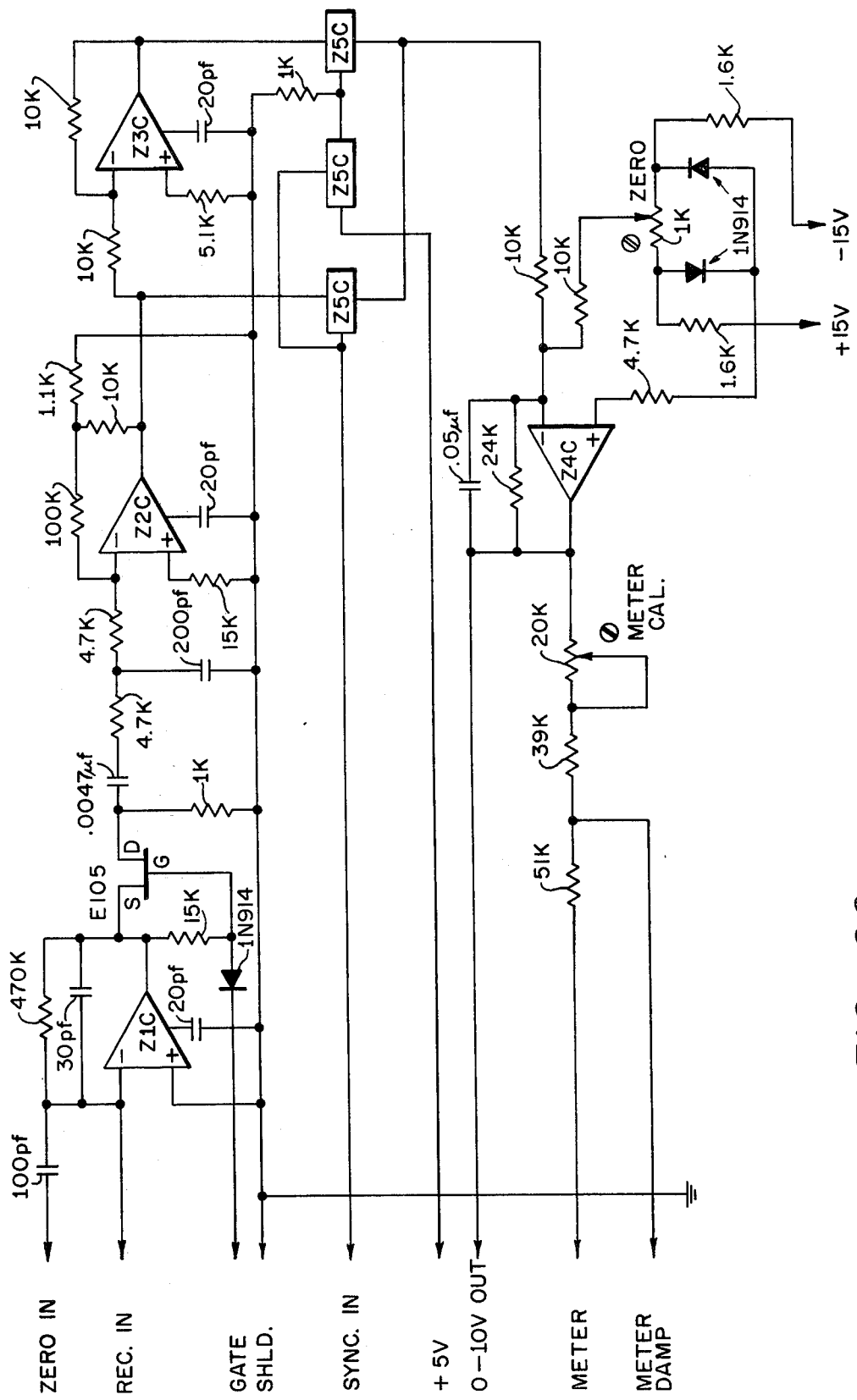

FIG. 9B is a schematic of the Switching Assembly. The function of the Switching Assembly is to connect each electrode plate of the sensor to 30 KHZ (XMIT IN), Receiver Assembly (REC OUT) or to ground (GND). The switching functions are accomplished by Quad FET switches Z1B-Z7B, Z15B and Z16B. Two switches are cascaded for each transmit or receive function for adequate isolation. The selection logic consists of triple-three input Nor gates Z11B-Z14B and Hex Inverters Z8B-Z10B. The logic is arranged so that when one Electrode Select Line is high, the associated electrode plate is connected to 30 KHZ for transmit and the preceding and following plates are connected to ground. The remaining plates are connected to the Receive line since without excitation from an Electrode Select Line as transmit on ground, the plate is automatically connected to the Receive line. Diodes are provided to prevent accidental over-voltaging from sensor connections. The resistances in FIG. 9B are are preferably 47K, the diodes IN914. The FETS Harris HI-1-201-5.

FIG. 9C is a schematic diagram of the Receiver Assembly. The zeroing voltage (ZERO IN) from the Driver Assembly (FIG. 9A) is applied to a 100 picofarad capacitor which produces a capacitive current into the Summing Junction of operational amplifier Z1C 180° out of phase with the capacitive current entering the summing junction from the sensor via the Switching Assembly (REC IN). The capacitor in the feed-back loop of Z1C converts the summed input currents into a voltage and shift the voltage into phase with the oscillator and also the SYNC IN from the Driver Assembly. The FET (E105) is shut off during plate sequence commutations by a negative GATE from the Driver Assembly. This is done to prevent saturation of the following operational amplifier Z2C by commutation spikes.

Z2C provides voltage amplification and operational amplifier Z3C acts as a unity gain inverter. The inverted and non-inverted signals are connected through two FET switches of the quad switch Z5C. The two switches are alternatively turned on by the SYNC signal to provide synchronous rectification of the signal. The third section of Z5C is connected to provide an inverted SYNC signal for the "inverted signal" switch.

Operational amplifier Z4C provides DC gain for the rectified signal and a low impedance output to both drive a meter and provide a 0–10 volt output proportional to the volume of the sensor occupied by the solid or liquid being measured. A ZERO control on the board is used to remove any DC offsets incurred in the circuitry and the METERCAL allows the full scale of the meter to be adjusted at exactly 10 volts.

Meter damping is provided by a switch (FIG. 1) with positions of none, 1 second and 2.5 second time constants.

Referring now to FIGS. 5-8, the mechanical configuration of the sensor assembly may comprise two semicircular tube laminates shown at 1 consisting of a conductive ground plane 2, an insulating layer 3 onto or into which conductive sensor plates 4 are fastened and to which electrical connections are accomplished by conductors 5 which pass through the insulator layer and connect to or are part of the isolated conductor of coaxial connectors 6 which are fastened to the ground plane.

Two semicircular tube laminates comprise the sensor which surrounds the outside periphery of an electrically transparent (non-conductive) section of flow tube 7 inside which the material being monitored 8 flows.

These semicircular sections are fastened over the flow tube utilizing clamps 9 the size of the laminate allowing intimate contact to the outer surface of the flow tube and providing minimal gap 10 at the adjacent edges of the sections. Placement of the sensor plates are symmetrical about the flow tube diameter and their axial length is such that the ends be sufficient distance within the guarded insulated laminate to eliminate external electrical disturbances, i.e., one inch plus.

These features being accomplished yields the precisely positioned sensor plate array required to accomplish the measurement described yet retain ease of attachment and portability.

It is evident that those skilled in the art, once given the benefit of the foregoing disclosure, may now make numerous other uses and modifications of, and departures from the specific embodiments described herein without departing from the inventive concepts. Consequently, the invention is to be construed as embracing each and every novel feature and novel combination of features present in, or possessed by, the apparatus and techniques herein disclosed and limited solely by the scope and spirit of the appended claims.

What is claimed is:

1. Method of measuring phase fractions in mixed flow media of dielectric material, comprising the steps of applying a cyclic series of relatively displaced voltage fields across the flow in distributed, spatially overlapping, time sequenced, fashion, each with a field of said series being established in tapered form between a relatively narrow input electrode opposing a relatively broad receiving electrode, summing capacitive currents so produced across the flow by such fields and affected by the flowing medium dielectric constant to produce a signal correlatable with phase fraction of the flow with direction dependent variations averaged out.

2. Method in accordance with claim 1 wherein the capacitive measurements are applied with a peripheral spread of the voltage field of at least 90° at one side.

3. Apparatus for practice of the method of claim 2 comprising means defining a peripheral array of capacitor electrodes around the flow path, a single phase high frequency oscillating voltage source, and means for applying the voltage sequentially to the electrodes to establish such field, in distinct steps, means for measuring currents produced through plates, and means for summing the measured currents to produce a phase fraction signal.

4. Apparatus in accordance with claim 3 wherein the means for applying are constructed such that as each electrode is sequentially excited as an input plate, at least one adjacent electrode is grounded and a multiplicity of non-adjacent electrodes are excited as receive electrodes relative to the transmit electrode.

5. Apparatus in accordance with claim 4 wherein a peripheral array of six evenly spaced circularly arranged, similar width electrodes is provided with three electrodes spanning substantially 180° of arc of the circle being excited as receive electrodes at any given time and opposing a simultaneously excited transmit electrode.

6. Apparatus in accordance with claim 3 wherein the means for measuring and summing comprises means for synchronous rectification of the summed currents to produce a d.c. measuring signal from the high frequency oscillation applied to the sensor.

7. Apparatus in accordance with claim 3 wherein the means for applying comprises means for shutting off the electrode supply during sequencing commutations.

8. Apparatus in accordance with claim 3 wherein the means for applying comprises cascaded Field Effect Transistors to isolate electrodes.

9. Apparatus in accordance with claim 3 wherein the electrodes are mounted in a tubular shell emplaceable over an electrically non-conductive tubular portion of a conduit for the flow to be measured.

* * * * *